United States Patent
Rabbitt et al.

(10) Patent No.: US 8,102,182 B2
(45) Date of Patent: Jan. 24, 2012

(54) SYSTEMS AND METHODS FOR MEASURING THE ELECTRICAL PROPERTIES OF A MICROPARTICLE

(75) Inventors: Richard D. Rabbitt, Salt Lake City, UT (US); Sameera Dharia, San Diego, CA (US)

(73) Assignee: University of Utah Research Foundation, Salt Lake City, UT (US)

( * ) Notice: Subject to any disclaimer, the term of this patent is extended or adjusted under 35 U.S.C. 154(b) by 579 days.

(21) Appl. No.: 12/249,643

(22) Filed: Oct. 10, 2008

(65) Prior Publication Data

US 2009/0096470 A1    Apr. 16, 2009

Related U.S. Application Data

(60) Provisional application No. 60/998,873, filed on Oct. 11, 2007.

(51) Int. Cl.
*G01N 27/02* (2006.01)
(52) U.S. Cl. ..................... 324/693; 324/76.11
(58) Field of Classification Search .................. 324/693, 324/600, 450–453; 600/547
See application file for complete search history.

(56) References Cited

U.S. PATENT DOCUMENTS

| | | | |
|---|---|---|---|
| 5,807,272 A * | 9/1998 | Kun et al. ...................... | 600/547 |
| 6,501,984 B1 | 12/2002 | Church et al. | |
| 6,940,286 B2 | 9/2005 | Wang et al. | |
| 7,169,107 B2 | 1/2007 | Jersey-Willuhn et al. | |

FOREIGN PATENT DOCUMENTS

| | | |
|---|---|---|
| EP | 1347706 | 10/2003 |
| WO | WO 02/053029 | 7/2002 |
| WO | WO 03/071140 | 8/2003 |

OTHER PUBLICATIONS

A R A Rahman et al., Cell culture monitoring by impedance mapping using a multielectrode scanning impedance spectroscopy system (Cell Map). Physiol. Meas. 29 (2008) S227-S239.
Abdur Rub Abdur Rahman et al., A micro-electrode array biosensor for impedance spectroscopy of human umbilical vein endothelial cells. Sensors and Actuators B 118 (2006)115-120. www.elsevier.com/locate/snb.
K.T.C. Chai et al., Electrical impedance tomography for sensing with integrated microelectrodes on a CMOS microchip. Sensors and Actuators B 127 (2007) 97-101. www.elsevier.com/locate/snb.

* cited by examiner

*Primary Examiner* — Vincent Q Nguyen
(74) *Attorney, Agent, or Firm* — Thorpe North & Western LLP

(57) ABSTRACT

A method of measuring the electrical properties of a microparticle is provided, which can include multiple steps. Steps can include situating the microparticle within an array of electrodes submerged in a conductive medium so that the microparticle and electrodes are in electrical communication when the electrodes are energized, and delivering an electrical signal into the medium from one electrode to an immediately adjacent electrode. High frequency signals can be used to penetrate the microparticle boundary and characterize the same, and low frequency signals can be used to characterize the shape and orientation of the microparticle. Characterization can be carried out by measuring the impedance affecting the current using at least one of a remaining electrode in the array.

1 Claim, 1 Drawing Sheet

SYSTEMS AND METHODS FOR MEASURING THE ELECTRICAL PROPERTIES OF A MICROPARTICLE

The present application claims the benefit of U.S. Provisional Patent Application No. 60/998,873, filed on Oct. 11, 2007, the entirety of which is incorporated herein by reference.

GOVERNMENT RIGHTS

This invention was made with government support under NIH Grant # R01 DC004298 awarded by the National Institutes of Health, and under NSF IGERT Grant # DGE9987616 awarded by the National Science Foundation. The Government has certain rights to this invention.

BACKGROUND

Inhomogeneous distributions of ion channels, lipids, and carbohydrates in and on a cell membrane contribute to biophysical mechanisms of controlling single cell physiology. Fluorescence imaging, patch-based and whole-cell electrophysiology, differential scanning calorimetry, freeze fracture microscopy, and atomic force microscopy are some of the tools which have been used to provide information about cell membrane organization. These techniques are good at visualizing single proteins, measuring whole cell kinetics, or creating nanometer sized profiles of the membrane surface. However, an effective method for determining the local functional organization around a living cell membrane with temporal resolution has remained a challenge. Therefore, a need remains to develop methods to characterize the localized composition and dynamic attributes of living cells, particularly the cell membrane, and thereby increase our understanding of cellular physiology.

BRIEF DESCRIPTION OF THE DRAWINGS

Additional features and advantages of the invention will be apparent from the detailed description which follows, taken in conjunction with the accompanying drawings, which together illustrate, by way of example, features of the invention. It is noted that the drawings are not necessarily to scale.

DETAILED DESCRIPTION

Figure 1:
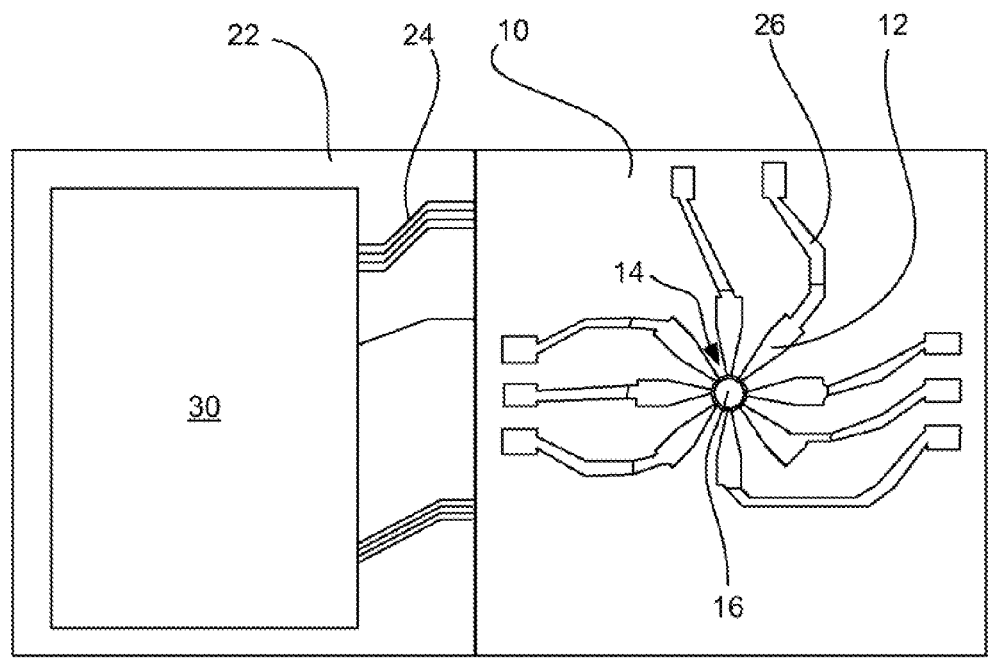
FIG. 1 shows a schematic for a device for measuring the electrical properties of a microparticle, such as a small particle or cell; the device including both an array of electrodes and a circuit board to facilitate analysis.

Reference will now be made to the exemplary embodiments of the present invention, both those described and those illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

In describing and claiming the present invention, the following terminology will be used in accordance with the definitions set forth below.

The singular forms "a," "an," and, "the" include plural referents unless the context clearly dictates otherwise.

The term "microparticle" as used herein refers to a small microparticle that is suitable for analysis with microscale electric impedance topography, particularly particles that can be conveniently measured in micrometers. For example, particles ranging from 1 to 1500 micrometers when measured along the smallest length or width of the particle would be considered microparticles in accordance with embodiments of the present invention. As used herein, a microparticle may be any inanimate particle of artificial or natural origin, including frozen or dead cells. However, the term "microparticle" also refers to living cells, tissue samples, tissue cultures, groups of cells, and other small organisms.

The term "boundary" not only refers to the outermost surface of a microparticle, but also refers to a depth just beneath the surface of the microparticle that is of interest to study. For example, the boundary of a cell may include not only the outermost surface, but also the cellular membrane as well as intracellular material just beneath the cellular membrane that interacts with the membrane itself.

As used herein, a plurality of items, structural elements, compositional elements, and/or materials may be presented in a common list for convenience. However, these lists should be construed as though each member of the list is individually identified as a separate and unique member. Thus, no individual member of such a list should be construed as a de facto equivalent of any other member of the same list solely based on their presentation in a common group without indications to the contrary.

Frequencies, amounts, voltages, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

The membrane of a cell is a complex structure that both maintains the intracellular milieu and regulates the interaction between intracellular and extracellular space. A major aspect of a cell's physiological state at any given time is the state of its electrochemical equilibrium. In this regard, the membrane acts as a complex electrical component, exhibiting both a large capacitative element (the lipid bilayer, charged molecules embedded in the membrane) and various conductances (ion transport across the cell membrane) whose respective values change in response to electrical stimuli, chemical stimuli, and the cell's native physiological activities. These changes are often largely due to conformational changes undergone by membrane proteins. Therefore, effectively characterizing the structure and electrical properties of the membrane of a living cell is valuable to understanding cellular function. The present disclosure provides methods that allow for the production of impedance-based images of the cell membrane with localized spatial resolution. This technology can complement current methods of cell membrane visualization and electrophysiology to provide a better understanding of the sub-cellular attributes of membrane function.

A device for creating an impedance-based image of a cell membrane—or, alternatively, the boundary of an inanimate microparticle, tissue sample, tissue culture, or groups of cells—can comprise a plurality of electrodes situated around a recording channel so that pairs or groups of the electrodes can be used to provide current or voltage to an microparticle situated in the recording channel, and also to take measurements therefrom. The electrodes may be arranged adjacently to one another, and in the same embodiment or in another embodiment, radially with respect to the microparticle, so that the tip of each electrode is oriented toward a central point in the array. In one embodiment, the array can be substantially positioned circumferentially or spherically around the microparticle. If the microparticle is not generally spherical in shape, the array can be adjusted accordingly to study various aspects of the microparticle boundary (or slightly therebeneath). In another embodiment, the array can be planar. In yet another embodiment, the array can be cylindrical or rectangular or any given irregular shape. In another embodiment, the array can be disposed on the surface of a chamber in which the microparticle is situated. In one aspect thereof, the microparticle may be moving through said chamber. In still another embodiment, this device can be constructed at scale so as to allow each of the electrodes to be in very close proximity to a single cell or other microparticle placed in the recording channel, without actually touching the boundary of the microparticle, with only a small volume of conductive fluid therebetween.

In accordance with this embodiment, a microscale device comprises planar electrodes that each lead to a central recording channel. The recording channel can be from about 0.005 mm to about 10 mm in diameter. In a particular embodiment, the channel has a diameter so as to accommodate only one microparticle. The electrodes themselves are from about 1 μm to about 1000 μm wide at the channel opening. The distance between the tip of the electrodes and the outermost surface of the microparticles is typically from about 0.0001 μm to about 10 μm, though actual contact can also occur, as long as there can be detectable electrical communication between the tip of the electrodes and the surface of the microparticles. In one embodiment, in order to allow the electrode tips to be small enough so that all of them can fit around the recording channel and also achieve a low electrode interface impedance, the electrodes can be generally recessed and triangular in shape or have an extended thickness. The electrodes and recording channel may be situated on a platform fabricated by rapid-prototyping, microfabrication, and electrochemical techniques known to the pertinent arts. For example, the arrangement of electrodes and the recording channel may be designed using computer-aided design software, and can be patterned onto a substrate material suitable for supporting electronic circuitry. The microparticle and the electrode tips are placed in electrical communication with each other, typically by submerging both in a conductive medium. In one embodiment, a gasket layer made of a nonconductive material is laid on top of the electrode array. In this layer, a well is fabricated to accommodate placement of the microparticle and allow for electrical communication with the electrodes themselves. In another embodiment, planar electrode arrays can be stacked to form a cylinder or other surface enclosing a volume.

An exemplary embodiment of such a device is shown in FIG. 1. On an array substrate 10, a number of electrodes 12 are arranged (eight in this embodiment) so that they define a central recording channel 14 in which a microparticle 16 may be placed for analysis. The electrodes are each electrically fed by corresponding trace elements 26. The microparticle may be an inanimate microparticle, a tissue sample, or a living cell such as an oocyte shown in this exemplary embodiment. In one embodiment, a gasket layer is laid over the electrodes to provide electrical insulation, while a well cut into the gasket allows for access to the electrodes and placement of the microparticle to be analyzed. In a typical embodiment, the well is filled with a conductive liquid medium. To provide for the delivery of signals to and collection of data from the microparticle, the array substrate can be attached to a circuit board 22 which includes an analysis circuit 30. The circuit board can include etched leads 24, each connecting an electrode though its corresponding trace element (connection not shown) on the array substrate.

Figure 2:
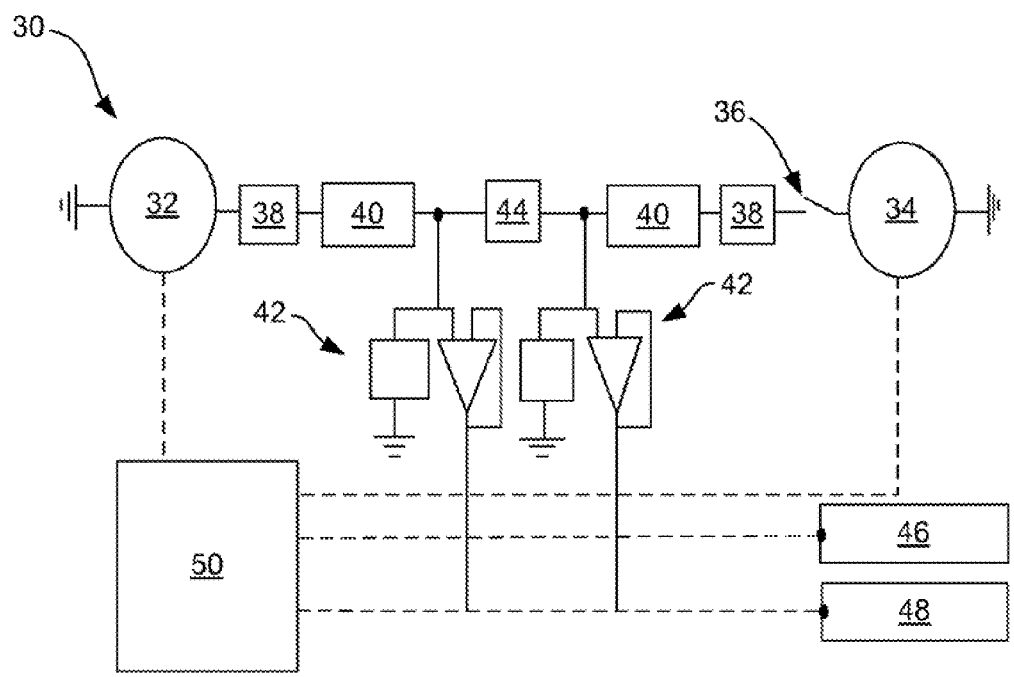
FIG. 2 shows a detailed schematic of an analysis circuit that can be used in the device of FIG. 1.

A schematic of an exemplary analysis circuit 30 is shown in FIG. 2. In one implementation of the system, stimulus signals are generated by a positive source 32 and a mirror negative source 34. The signals produced by these two sources are typically 180 degrees out of phase. Other implementations of this circuit include a signal being sent from either the positive or negative source while the other signal input is grounded. Onset of the signal is triggered by closing an open circuit switch 36. The signal from each source is passed through a reference impedance 38 and then a digital switch 40 that is used to select the lead 24 down which the signal will be sent. Operational amplifiers 42 measure the voltages detected by both the positive source and mirror negative source. The reference impedance is used to calibrate any leak across the operational amplifiers and also used in calculating the recording channel impedance 44. Measurement signals are sent to lock-in amplifiers 46 and a digital oscilloscope 48. A controller 50 with a general purpose interface bus coordinates stimulus and recording.

The present invention also provides methods for imaging the shape and/or electrical properties of a structural boundary of a microparticle to some finite depth. Microscale electric impedance topography can successfully be used to measure the local dielectric properties of a cell membrane or inanimate particles using fringe field electrical signals. In the case of living cells, these methods may be used to characterize the cell membrane.

Such methods can utilize a device similar to the device disclosed above. It should be noted that, while the discussion herein will primarily emphasize interrogation of a cell, this is only for convenience of describing aspects of the disclosure. However, it is understood that discussion of a cell can be analogous to discussion of other types of microparticles, and discussion of a cell membrane can be analogous to the boundary of other types of microparticles. Thus, in accordance with these methods, a single cell can be positioned between the electrodes, and electrical recordings are made by either pairs or groups of electrodes. A difference-based or other reconstruction algorithm is used to map this data into an impedance distribution of a single cell's membrane. Impedance measurements generated from interrogating the cell with low-frequency (~1 kHz-100 kHz) signals are used to create an image of the position and shape of the cell within a recording channel. At low frequencies the conduction current dominates, so that substantially all of the current is shunted in the extracellular space between the two interrogating electrodes. This occurs because the resistance of the plasma membrane is typically much greater than the surrounding media. While low-frequency fringe-field data may be less useful in elucidating information about the plasma membrane, intracellular organelles, or proteins, it can provide information about extracellular shunt path size and therefore can be used to estimate the shape of a cell in the chamber.

As interrogation frequency increases (e.g. 100 kHz-5 MHz), current is divided between displacement current in the plasma membrane and conduction current in the extracellular shunt path. The amount of current displaced across the membrane in this mid-frequency range can be used to estimate the effective impedance properties of the cell membrane (i.e. passive permittivity and active components). Measurements made in this frequency range can also be used to detect dielectric change in membrane impedance associated with, as an example, protein conformational change in response to an excitatory stimulus applied to the cell. It should be noted that if the extracellular shunt path is too large, the corner frequency can quickly exceed values at which membrane interrogation is practical using this approach. It may therefore be advantageous to size the system so cells fit snugly within the chamber and are in close vicinity to the interrogating electrodes.

Impedance measurements generated from interrogating the cell with still higher frequency signals (~5 MHz-1 GHz) can be used to investigate intracellular organelle distribution or the effective dielectric relaxation time constants of proteins embedded in the cell membrane. At such frequencies, almost all of the current applied to the system is displaced across the cell membrane, and the membrane effectively becomes transparent to the applied radio-frequency signals. As such, intracellular organelle distribution might be calculated from the impedances measured in this high frequency range. In another application of this high frequency cellular interrogation, measurements made in this range can be used to excite mobile charge domains on the cell's surface. This information might be used to determine effective protein size on the surface of the cell membrane by estimating dipole relaxation time.

In accordance with the present invention, a method for measuring the electrical properties of a microparticle comprises interrogating the microparticle with radio frequency signals. A cell, group of cells, inanimate microparticle, or other small microparticle is placed in the recording channel of the device described above. In one embodiment, the microparticle is situated so that none of the electrodes come into physical contact with it, so that electrical contact between the microparticle and the electrodes is established solely by the medium in which they are submerged. In an alternate embodiment, the microparticle is situated so that it is touched by one or all of the electrodes to be utilized.

The cell is then interrogated by delivering a high-frequency electrical signal into the medium from one electrode to an immediately adjacent electrode. In another embodiment of a microscale electric impedance topography system, signals can also be applied to/measured from groups of electrodes or nonadjacent pairs of electrodes. In one embodiment, the signal applied to the electrodes includes a sinusoidal signal. The mutual proximity of the electrodes results in an electric fringe field interaction between the microparticle and the incoming signal, the intensity of which falls off sharply with distance. As a result of this mode of delivery, some of the resulting current passes through the outer boundary of the microparticle, but only to a limited depth. In a particular aspect, the signal frequency is from about 100 kHz to about 10 GHz. In one embodiment, the signal frequency can be from about 100 kHz to about 5 GHz, and in another embodiment, the signal frequency can be from about 5 MHz to about 1 GHz. The penetration of the field into the microparticle causes a detectable disturbance in the field that is indicative of the microparticle's dielectric properties. The amount of current displaced across/through the microparticle will depend on the microparticle's electrical properties and the frequency range of stimulation should be determined based on these values. During microparticle stimulation, other electrodes in the array can simultaneously be used to make measurements of the impedance encountered by the current. In a particular embodiment, impedance measurements are made between adjacent electrode pairs, and this is done for all adjacent pairs of electrodes in the array. The measurements taken at each electrode over the course of the interrogation regime may then be averaged and plotted to generate an impedance-based representation of the microparticle outer layer.

Interrogation of the microparticle with lower-frequency signals, e.g. from about 1 kHz to about 100 kHz for a microparticle whose resistance is similar to a cell membrane, provides a different result, due to the fact that these signals predominantly pass around the microparticle rather than penetrating it. A plot of the real component of the measured impedance as measured by each electrode will then represent the shape of the microparticle in the channel. As such, this approach provides a method of characterizing the shape of the microparticle as well as its position in the recording channel.

Data can be shown in a variety of ways. In one way, measurements from both low-frequency and high-frequency interrogation may be plotted together in a unit circle graph that represents the recording channel, with the magnitude of each impedance measurement represented by distance from the center of the plot. Either the real component or the imaginary component of impedance may be plotted. This provides one way of visualizing the electrical characteristics of a microparticle. For example, the plots of imaginary impedance for a microparticle with an electrically uniform outer layer will exhibit a relationship between the low- and high-frequency measurements that is uniform around the outer layer. Spatial variation in the relationship, however, indicates that the boundary exhibits spatial variation in its electrical properties. In a particular embodiment of the present invention, a microparticle may be situated within a stack of more than one planar electrode array, so that a three-dimensional electrical representation of the microparticle may be obtained.

The task of estimating microparticle impedance is complicated by the fact that every calculated chamber impedance actually consists of at least two impedances: (1) double layer impedances across each stimulating/recording electrode, and (2) the impedance of the microparticle in the recording channel. Therefore, using microscale electric impedance topography can benefit from ways to calculate or estimate the double layer or to differentially subtract the double layer impedance out of the chamber impedance calculation. The present disclosure provides ways in which to find a good estimate of the impedance of the microparticle in the recording chamber. One way to isolate the double layer impedance component from the microparticle's impedance component is to assume that the medium in which the microparticle is located has a much lower impedance than the microparticle itself. Based on this assumption, one can make two measurements. The first measurement can be of only the medium in the recording channel at a particular frequency and peak stimulation voltage. The second measurement can be of both the medium and the microparticle in the recording channel using the same parameters as the first measurement. Since both measurements are done in the same solution, the double layer impedance in both cases should be equal. If the media impedance is much less than the microparticle impedance, then subtracting both of these measurements will result in a value which is very close to that of the microparticle impedance. One caveat of this approach is that it also subtracts the electrical resistance of the media itself, and therefore the real component of the impedance is shifted by a real-valued constant.

An additional method of separating double layer impedances from microparticle impedances is also provided, in which it is unnecessary to make assumptions about the impedance of the medium. This method can provide fairly accurate values of individual double layer impedances for a microscale electric impedance topography device, particularly in low noise conditions. This method can be extrapolated to any system which has at least three individually voltage controllable electrodes. While an exemplary embodiment of this method using three electrodes will be described, the concept can be extrapolated to any number of electrodes. In the three electrode embodiment, measurements are made between pairs of electrodes and all permutations (group) using a spatially (e.g., radially) arranged three electrode set, designated $E_1$-$E_3$. There are six unknowns in this system: the solution impedance values between each pair of electrodes ($Zs_{1-3}$) and the double layer impedance for each of the electrodes themselves ($Zd_{1-3}$). A signal is applied between each of the possible electrode pairs in the three electrode set, i.e. $E_1$-$E_2$, $E_1$-$E_3$, and $E_2$-$E_3$, with one electrode receiving a signal from a positive voltage source and the other receiving the mirror negative voltage. An impedance measurement is taken for each pair. Signals are then applied and impedance measurements are made between each individual electrode and the remaining pair of electrodes shorted together to cover all permutations, i.e. between $E_1$+$E_2$ and $E_3$; between $E_1$+$E_3$ and $E_2$; and between $E_2$+$E_3$ and $E_1$. Each individual recording configuration has an lumped parameter circuit model associated with it, and each circuit model includes some of the impedance components of interest (either $Zs_{1-3}$ and/or $Zd_{1-3}$). In the case of a group of 3 electrodes, the outcome of every individual recording would result in impedance measurements which can be represented by 6 equations. In another embodiment, more than 3 electrodes is used to arrive at an over-determined set of equations for all permutations of electrodes. A nonlinear parameter estimation can be used to best fit parameters for all equations given the actual chamber impedance measurements. In a particular embodiment, the Levenberg-Marquardt method can be used. The three electrode method can also work in finding additional double layer and solution impedance values for cases in which there are additional electrodes. For every electrode added, a minimum of two unknown solution impedances and one unknown double layer impedance are added. In these cases, by including at least three additional pairwise and groupwise recording schemes, all the unknown variables can be solvable. Any information beyond the three extra recordings can be used to reduce error in the nonlinear curve fit approximation.

The following examples illustrate embodiments of the invention that are presently known. Thus, these examples should not be considered as limitations, but are merely in place to teach how to make the best-known exemplary systems and methods of the present invention based upon current experimental data. As such, a representative number of systems and method of manufacture are disclosed herein.

EXAMPLES

Example 1

Fabricating a Microscale Electric Impedance Topography Device

Microscale electric impedance topography devices were designed using detailed drawings, and consisted of eight planar electrodes which lead to a central recording channel. The electrodes themselves were 150 microns wide at the channel opening, had a triangular shape and were evenly spaced around a recording channel measuring 1.1-1.2 mm in diameter. Each electrode was connected to a bond pad which acted as an interface between the device and signals to/from the board and to an electrode plating line on the outer edge of each device that connected all of the metal contacts together. Gasket layers were also designed to create wells above the electrodes and to insulate the electrodes from each other.

A double-layered polyester film (Rubylith, Ulano Corporation, Brooklyn, N.Y.) was chosen as the material on which to fabricate the devices. The Rubylith was patterned using a knife plotter (Graphtec America, Santa Ana, Calif.); the electrodes were patterned on the top layer of the polyester film, and the recording channel was patterned through both layers of polyester film. The electrode plots were weeded and this film was then sputtered with a chrome seed layer for 5 minutes at 100 W and platinum metal for 45 minutes at 50 W.

After sputtering, the top layer of the polyester film was removed, leaving a metallized clear polyester backing with electrodes sputtered on top of it. In order to reduce electrode impedance, the devices were then plated with platinum black. A plating line had been drawn around the periphery of the device to allow for uniform plating of every electrode. Each device was held in the platinum black plating solution for 30 seconds with 10 mA of current. A four inch platinum wafer was used as the counter electrode. All parts of the device in which plating was not desired were protected with polyimide adhesive tape (Kapton, Du Pont, Inc., Wilmington, Del.).

In order to further reduce double layer impedances, a well was made above the triangulated portion of every electrode that lead to the central recording channel. For well construction, three layers of polyimide adhesive tape were stacked together and patterned on the knife plotter. These were manually aligned and carefully placed on a plated device. A final layer of polyimide adhesive tape was also cut so that it could cover all of the wells, and only had the recording channel hole patterned into it. This gasket was placed on top of the previous tape layer with the use of a stage microscope. All wells were then filled with an appropriate medium (e.g. physiological saline or oocyte media) using a microfiller. The addition of a well above each electrode could be used to reduce the electrode double layer impedance by increasing the area of each electrode in contact with a electrolytic solution.

The electrode array was clamped in a polycarbonate interface that allowed for cell loading and positioning (via a vacuum port) into the recording chamber. The bond pads on the electrode array contacted the PCB through a series of spring-loaded gold pins (B1363-D4 Interface Contacts, Rika Denshi, Attleboro, Mass.). The electrical source consisted of either arbitrary wave form generators (Tektronix AFG320 or AWG430, Tektronix, Beaverton, Oreg.). Each source was individually calibrated using a Thévenin equivalent model to compensate for load-dependent loss at frequencies greater than 100 kHz. A voltage-dividing on-board reference impedance was used to calculate recording-chamber impedance. High-impedance voltage-follower operational amplifiers (OPA366, Texas Instruments, Dallas, Tex.) located on the headstage PCB were used to sample the voltage drop across the reference impedance to determine current. All signals were recorded in quadrature by lock-in amplification (SR830/SR844, Stanford Research, Sunnyvale, Calif.). Electrodes on the array were individually addressable, and the interrogating signal was directed to the electrode of interest using Max4521 digital switches (Maxim Integrated Products, Sunnyvale, Calif.) located on the headstage PCB. Source output, signal recording, and electrode pair selection were automatically controlled via a custom computer interface (IGOR Pro, WaveMetrics, Portland, Oreg.). The program remotely controlled the waveform generator and lock-in amplifier recording (IEEE 488 General Purpose Interface Bus, National Instruments, Austin, Tex.). Analog voltage sampling and digital switching were controlled via 16-bit analog-digital converters and digital outputs (ITC 1600, HEKA Inst., Bellmore, N.Y.).

Example 2

Characterizing the Shape and Electrical Properties of a Glass Disk

The device of Example 1 was used to characterize glass microparticles. In each experiment, a toroidal glass washer (850-1000 µm) was placed within the planar circular array of electrodes in the device of Example 1 and immersed in physiological saline. The disk was interrogated by delivering a sinusoidal signal to each pair of adjacent electrodes in the array, while the remaining electrodes in the array took impedance measurements. Two pairs of signal frequencies were used: (a) 10 kHz, then 100 kHz; and (b) 10 kHz then 1 MHz. The individual washer data was rotated so that a statistical analysis could be performed on multiple washers, and a second order Fourier series representation of each washer was averaged together. To estimate the contribution of the electrode-electrolyte double-layer impedance, data were also collected under the same stimulus conditions when the chamber was only filled with extracellular media (media-only condition) during each experiment.

After subtracting the double-layer impedance, the impedance measured between adjacent electrode pairs was divided in half and assigned to chamber positions that corresponded to center point directly in front of each interrogating electrode. This was done for every electrode pair measurement, and the values associated with each electrode position were averaged together. The procedure resulted in impedance data for 8 locations around the circumference of the cell corresponding to the 8 electrode positions in the circular array. Impedance data were interpolated between electrodes and smoothed using a five-term Fourier series in the form $$Z(\vartheta) = \sum_{n=0}^{5} (A_n \cos(\vartheta - \vartheta_0) + B_n \sin(\vartheta - \vartheta_0)).$$

$A_n$ and $B_n$, calculated from the data using a least squares regression, are complex-valued Fourier coefficients. Z is the interpolated impedance as a function of polar angle $\vartheta$.

The representation for real impedance for both frequencies was then plotted in a unit circle that represented the recording channel, and then the same was done for imaginary impedance. Impedance plots for each phantom were first constructed using $\theta_0 = 0$, and subsequently rotated by angle $\theta_0$ to align the phantom major axis with the horizontal. The major axis was identified using a photomicrograph of the phantom in the chamber. These rotated results were then averaged across phantoms. Means and standard errors were plotted as a function angle $\theta_0$. Unpaired, Student's t-tests were used to compare the major and minor axis lengths of the toroidal glass phantoms.

The shape of each of the plots corresponded to the shape and orientation of the washer. The plots of imaginary component of the impedances for 10 kHz and 100 kHz were substantially superimposed over their whole circumference. The plots of imaginary impedances for 10 kHz and 1 MHz showed markedly different magnitudes, but the difference was uniform over the whole circumference. These results indicated that the dielectric properties of the washer were uniform, as expected for a glass washer.

Example 3

Characterizing the Shape and Electrical Properties of an Oocyte

The device of Example 1 was used to characterize oocytes of *Xenopus laevis*. Each oocyte was placed within the planar circular array of electrodes in the device of Example 1 and immersed in a conductive solution. Each oocyte was depolarized using a two-microelectrode system (AxoClamp2B, VG-10MGU, CA HS-1 LU, Molecular Devices, Sunnyvale, Calif.). Glass micro-pipettes were filled with 3 M KCl and had a nominal access resistance of ~3 MΩ. Step depolarization stimuli were applied with duration 250-500 ms, and cells were depolarized between 15-40 mV. The current/voltage responses were averaged over ~100 stimulus presentations.

(a) Measuring dynamics of impedance and capacitance. Simultaneously, the device was used to measure fringe-field impedance from both hemispheres of the oocyte using a 700 kHz pairwise interrogation. Cell position and orientation in the electrode array were random, so any differences found between excitability of the two hemispheres could not be attributed to systematic errors in the measurement system. For the purpose of comparing fringe-field impedance at rest to that during membrane depolarization, the analog lock-in signals (in quadrature) were low-pass filtered at ~33 Hz and averaged separately over 1) the entire period of rest and 2) the entire period of depolarization. Resting and depolarized voltage data were used to estimate the change in effective membrane capacitance for the two hemispheres of the cell (700 kHz interrogation frequency, electrode area ~200 µm*163 µm, passive capacitance $C_{membrane} = 4$ µF/cm$^2$). Unpaired, two-tailed, Student's t-tests (n=5) were used to compare 1) voltage magnitude changes for data collected at rest to data collected during depolarization for an oocyte and 2) impedance magnitude change during depolarization between either hemisphere of an oocyte. In certain cases, exponentials were observed in the voltage data traces which could be attributed to the kinetics of particular voltage-dependent ion channels.

(b) Characterizing oocyte shape. The procedure to measure and plot $Z(\theta)$ described in Example 2 was also used for the oocytes. For each oocyte, a photomicrograph taken during microscale electric impedance topography interrogation was used to rotate the data by an angle $\theta_0$ (see Fourier series in Example 2) so that the meridian separating the animal and vegetal hemispheres for a particular cell was aligned with the horizontal. This allowed for alignment of the gross morphology of different oocytes and comparisons across cells. Real and imaginary components of Z were plotted in polar form to map the impedance as a function of position around the circular electrode array. Means and standard errors were determined across multiple cells, thus providing confidence intervals as functions of angular position around the cell. Unpaired Student's t-tests were used to compare spatial differences between the two hemispheres of the oocyte.

The shape of each of the plots roughly corresponded to the shape of the oocyte. The plots of the imaginary component of the impedances for both the 10 kHz/100 kHz comparisons and the 10 kHz/1 MHz comparisons showed differences between low-frequency and high-frequency measurements whose magnitude was different for the animal and vegetal halves. These results indicated that the dielectric properties of the membrane on the two halves of the oocyte were quite different.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

The invention claimed:

1. A device for measuring the electrical properties of a microparticle, comprising:
   (a) an array substrate situated on a circuit board;
   (b) an array of electrodes patterned on a surface of the array substrate and arranged to as to define a substantially centrally located recording channel;
   (c) a gasket layer of electrically nonconductive material laid on top of the array, and having a well defined by an opening in the gasket layer situated over the recording channel;
   (d) circuitry on the circuit board, said circuitry comprising a voltage source and digital switches to allow voltage to be applied to selected electrodes; and
   (e) an interface connecting each electrode to the circuitry.

* * * * *